(12) United States Patent
Thompson et al.

(10) Patent No.: US 9,814,828 B2
(45) Date of Patent: Nov. 14, 2017

(54) METHOD AND APPARATUS FOR PREPARING AND MONITORING AN INTRAVENOUS FLUID BAG

(71) Applicant: Aesynt Incorporated, Cranberry, PA (US)

(72) Inventors: Jeff Thompson, Allison Park, PA (US); David Deutsch, Cranberry Township, PA (US); Preeti Churbock, Pittsburgh, PA (US); Kevon Garrison, Rocky Point, NC (US); John Barickman, West Chester, PA (US); Bruce Thompson, Pittsburgh, PA (US); Randy Rossi, Greensburg, PA (US); Gregoire Aby-Eva, Pittsburgh, PA (US)

(73) Assignee: Aesynt Incorporated, Cranberry, PA (US)

( * ) Notice: Subject to any disclaimer, the term of this patent is extended or adjusted under 35 U.S.C. 154(b) by 864 days.

(21) Appl. No.: 13/837,240

(22) Filed: Mar. 15, 2013

(65) Prior Publication Data
US 2014/0278156 A1    Sep. 18, 2014

(51) Int. Cl.
*A61J 1/18*   (2006.01)
*A61M 5/168*   (2006.01)
(Continued)

(52) U.S. Cl.
CPC ........ *A61M 5/1414* (2013.01); *A61M 5/1684* (2013.01); *A61M 5/16831* (2013.01);
(Continued)

(58) Field of Classification Search
CPC .. A61M 5/1483; A61M 2205/50; A61M 5/14; A61M 5/1413; A61M 2205/583;
(Continued)

(56) References Cited

U.S. PATENT DOCUMENTS 4,378,014 A * 3/1983 Elkow ................. A61M 5/1684
                                                128/DIG. 13
4,532,414 A * 7/1985 Shah ....................... A61M 5/44
                                                       165/46
(Continued)

*Primary Examiner* — Toan Le
*Assistant Examiner* — Jeffrey Aiello
(74) *Attorney, Agent, or Firm* — Alston & Bird LLP

(57) ABSTRACT

An intravenous (IV) fluid monitoring system and method are provided to facilitate notification that a replacement IV fluid bag should be prepared. In this regard, an IV fluid monitoring system includes a bag sensing element carried by an IV fluid bag. The IV fluid monitoring system further includes first and second sensing elements positioned on opposite sides of the IV fluid bag and configured to interact with the bag sensing element. The first and second sensing elements are physically separate from the IV fluid bag. The bag sensing element and the first and second elements are positioned such that a line of sight between at least the first sensing element and the bag sensing element extends through the IV fluid within the IV fluid bag while the IV fluid bag is in a filled state. A method and apparatus are also provided to facilitate preparation of an IV fluid bag.

20 Claims, 6 Drawing Sheets

(51) Int. Cl.
*A61J 1/00* (2006.01)
*A61M 5/14* (2006.01)

(52) U.S. Cl.
CPC .............. *A61M 2205/3306* (2013.01); *A61M 2205/3386* (2013.01); *A61M 2205/3561* (2013.01)

(58) Field of Classification Search
CPC . A61M 5/1411; A61M 5/16827; A61B 19/44; G01K 1/00; G01N 15/0205
USPC .................. 73/299, 861; 374/141, 150, 208; 604/246, 408, 65, 151, 500; 600/309
See application file for complete search history.

(56) References Cited

U.S. PATENT DOCUMENTS

| | | | |
|---|---|---|---|
| 4,717,042 A | 1/1988 | McLaughlin | |
| 4,785,969 A | 11/1988 | McLaughlin | |
| 4,847,764 A | 7/1989 | Halvorson | |
| 4,984,462 A * | 1/1991 | Hass, Jr. ................. | A61M 5/14 250/577 |
| 5,014,875 A | 5/1991 | McLaughlin et al. | |
| 5,135,485 A * | 8/1992 | Cohen ................. | A61M 5/1684 324/606 |
| 5,190,185 A | 3/1993 | Blechl | |
| 5,200,090 A * | 4/1993 | Ford ................... | A61M 1/3441 210/104 |
| 5,289,858 A * | 3/1994 | Grabenkort ............... | A61J 1/20 141/114 |
| 5,314,243 A | 5/1994 | McDonald et al. | |
| 5,346,297 A | 9/1994 | Colson, Jr. et al. | |
| 5,377,864 A | 1/1995 | Blechl et al. | |
| 5,405,048 A | 4/1995 | Rogers et al. | |
| 5,431,299 A | 7/1995 | Brewer et al. | |
| 5,460,294 A | 10/1995 | Williams | |
| 5,468,110 A | 11/1995 | McDonald et al. | |
| 5,480,062 A | 1/1996 | Rogers et al. | |
| 5,520,450 A | 5/1996 | Colson, Jr. et al. | |
| 5,563,584 A * | 10/1996 | Rader ............... | A61M 5/1684 128/DIG. 13 |
| 5,564,803 A | 10/1996 | McDonald et al. | |
| 5,593,267 A | 1/1997 | McDonald et al. | |
| 5,599,303 A * | 2/1997 | Melker ............. | A61M 5/16886 604/246 |
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |
| 5,745,366 A | 4/1998 | Higham et al. | |
| 5,761,877 A | 6/1998 | Quandt | |
| 5,776,105 A * | 7/1998 | Corn ................... | A61M 5/1483 604/174 |
| 5,797,515 A | 8/1998 | Liff et al. | |
| 5,805,456 A | 9/1998 | Higham et al. | |
| 5,842,976 A | 12/1998 | Williamson | |
| 5,878,885 A | 3/1999 | Wangu et al. | |
| 5,880,443 A | 3/1999 | McDonald et al. | |
| 5,883,806 A | 3/1999 | Meador et al. | |
| 5,893,697 A | 4/1999 | Zini et al. | |
| 5,905,653 A | 5/1999 | Higham et al. | |
| 5,912,818 A | 6/1999 | McGrady et al. | |
| 5,927,349 A * | 7/1999 | Martucci ................ | A61J 3/002 141/104 |
| 5,927,540 A | 7/1999 | Godlewski | |
| 5,940,306 A | 8/1999 | Gardner et al. | |
| 5,971,593 A | 10/1999 | McGrady | |
| 6,003,006 A | 12/1999 | Colella et al. | |
| 6,011,999 A | 1/2000 | Holmes | |
| 6,021,392 A | 2/2000 | Lester et al. | |
| 6,039,467 A | 3/2000 | Holmes | |
| 6,065,819 A | 5/2000 | Holmes et al. | |
| 6,068,156 A | 5/2000 | Liff et al. | |
| 6,109,774 A | 8/2000 | Holmes et al. | |
| 6,112,502 A | 9/2000 | Frederick et al. | |
| 6,116,461 A | 9/2000 | Broadfield et al. | |
| 6,151,536 A | 11/2000 | Arnold et al. | |
| 6,170,230 B1 | 1/2001 | Chudy et al. | |
| 6,176,392 B1 | 1/2001 | William et al. | |
| 6,189,727 B1 | 2/2001 | Shoenfeld | |
| 6,223,934 B1 | 5/2001 | Shoenfeld | |
| 6,256,967 B1 | 7/2001 | Hebron et al. | |
| 6,283,322 B1 | 9/2001 | Liff et al. | |
| 6,289,656 B1 | 9/2001 | Wangu et al. | |
| 6,290,681 B1 * | 9/2001 | Brown .............. | A61M 5/16886 128/DIG. 13 |
| 6,338,007 B1 | 1/2002 | Broadfield et al. | |
| 6,339,732 B1 | 1/2002 | Phoon et al. | |
| 6,361,263 B1 | 3/2002 | Dewey et al. | |
| 6,370,841 B1 | 4/2002 | Chudy et al. | |
| 6,449,927 B2 | 9/2002 | Hebron et al. | |
| 6,471,089 B2 | 10/2002 | Liff et al. | |
| 6,497,342 B2 | 12/2002 | Zhang et al. | |
| 6,499,270 B2 | 12/2002 | Peroni et al. | |
| 6,532,399 B2 | 3/2003 | Mase | |
| 6,564,121 B1 | 5/2003 | Wallace et al. | |
| 6,581,798 B2 | 6/2003 | Liff et al. | |
| 6,609,047 B1 | 8/2003 | Lipps | |
| 6,611,733 B1 | 8/2003 | De La Huerga | |
| 6,625,952 B1 | 9/2003 | Chudy et al. | |
| 6,640,159 B2 | 10/2003 | Holmes et al. | |
| 6,650,964 B2 | 11/2003 | Spano, Jr. et al. | |
| 6,671,579 B2 | 12/2003 | Spano, Jr. et al. | |
| 6,681,149 B2 | 1/2004 | William et al. | |
| 6,742,671 B2 | 6/2004 | Hebron et al. | |
| 6,755,931 B2 | 6/2004 | Vollm et al. | |
| 6,760,643 B2 | 7/2004 | Lipps | |
| 6,776,304 B2 | 8/2004 | Liff et al. | |
| 6,785,589 B2 | 8/2004 | Eggenberger et al. | |
| 6,790,198 B1 | 9/2004 | White et al. | |
| 6,814,254 B2 | 11/2004 | Liff et al. | |
| 6,814,255 B2 | 11/2004 | Liff et al. | |
| 6,847,861 B2 | 1/2005 | Lunak et al. | |
| 6,874,684 B1 | 4/2005 | Denenberg et al. | |
| 6,892,780 B2 | 5/2005 | Vollm et al. | |
| 6,895,304 B2 | 5/2005 | Spano, Jr. et al. | |
| 6,975,922 B2 | 12/2005 | Duncan et al. | |
| 6,985,797 B2 | 1/2006 | Spano, Jr. et al. | |
| 6,996,455 B2 | 2/2006 | Eggenberger et al. | |
| 7,010,389 B2 | 3/2006 | Lunak et al. | |
| 7,014,063 B2 | 3/2006 | Shows et al. | |
| 7,016,766 B2 | 3/2006 | William et al. | |
| 7,040,504 B2 | 5/2006 | Broadfield et al. | |
| 7,052,097 B2 | 5/2006 | Meek, Jr. et al. | |
| 7,072,737 B2 | 7/2006 | Lunak et al. | |
| 7,072,855 B1 | 7/2006 | Godlewski et al. | |
| 7,077,286 B2 | 7/2006 | Shows et al. | |
| 7,085,621 B2 | 8/2006 | Spano, Jr. et al. | |
| 7,092,796 B2 | 8/2006 | Vanderveen | |
| 7,093,755 B2 | 8/2006 | Jordan et al. | |
| 7,100,792 B2 | 9/2006 | Hunter et al. | |
| 7,103,419 B2 | 9/2006 | Engleson et al. | |
| 7,111,780 B2 | 9/2006 | Broussard et al. | |
| 7,139,639 B2 | 11/2006 | Broussard et al. | |
| 7,150,724 B2 | 12/2006 | Morris et al. | |
| 7,171,277 B2 | 1/2007 | Engleson et al. | |
| 7,218,231 B2 | 5/2007 | Higham | |
| 7,228,198 B2 | 6/2007 | Vollm et al. | |
| 7,249,688 B2 | 7/2007 | Hunter et al. | |
| 7,348,884 B2 | 3/2008 | Higham | |
| 7,417,729 B2 | 8/2008 | Greenwald | |
| 7,419,133 B2 | 9/2008 | Clarke et al. | |
| 7,426,425 B2 | 9/2008 | Meek, Jr. et al. | |
| 7,554,449 B2 | 6/2009 | Higham | |
| 7,571,024 B2 | 8/2009 | Duncan et al. | |
| 7,588,167 B2 | 9/2009 | Hunter et al. | |
| 7,982,612 B2 | 7/2011 | Braun | |
| 2002/0021741 A1 * | 2/2002 | Faries, Jr. .............. | G01K 11/12 374/141 |
| 2002/0038392 A1 * | 3/2002 | De La Huerga .. | A61M 5/14212 710/8 |
| 2008/0275422 A1 * | 11/2008 | Ross ................... | A61M 5/1483 604/408 |

(56) References Cited

U.S. PATENT DOCUMENTS

| | | | | |
|---|---|---|---|---|
| 2011/0043357 A1* | 2/2011 | Peatfield | ............. | A61M 5/1413 |
| | | | | 340/522 |
| 2012/0226446 A1* | 9/2012 | Nelson | .................. | A61M 5/168 |
| | | | | 702/25 |
| 2012/0291627 A1* | 11/2012 | Tom | ..................... | B67D 7/0261 |
| | | | | 95/8 |

* cited by examiner

METHOD AND APPARATUS FOR PREPARING AND MONITORING AN INTRAVENOUS FLUID BAG

TECHNOLOGICAL FIELD

An example embodiment of the present invention relates generally to a method and apparatus for preparing and monitoring an intravenous (IV) fluid bag.

BACKGROUND

IV fluid bags are widely utilized to deliver fluid and medication to patients. In a hospital or other healthcare facility, the IV fluid bags may be prepared by a pharmacy at a location remote from the patient. The IV fluid bags may then be delivered to the healthcare practitioners responsible for the patient's care (hereinafter generically referred to as nurses). The IV fluid may then be administered to the patient. For example, the IV fluid bag may be hung upon an IV pole and fluidly connected for administration to the patient.

Once prepared, at least some IV fluid bags are required to be administered to a patient within a predefined time period. Failure to administer these IV fluid bags to a patient within the predefined time period may cause the IV fluid bags to become outdated and to no longer be acceptable for administration to a patient. As such, nurses must ensure that the IV fluid bags are administered in a timely fashion so as to avoid instances in which the IV fluid bags become outdated and the IV fluid is wasted. An IV fluid bag may sometimes be quite expensive, such as in instances in which the medication to be delivered via the IV fluid is expensive, such that the failure to administer IV fluid bags in a timely manner may undesirably increase the cost associated with patient care and decrease the efficiency with which patient care is provided.

The challenges associated with the timely administration of IV fluid bags may be particularly acute in an instance in which a patient receiving IV fluid requires the preparation of a replacement IV fluid bag to take the place of the current IV fluid bag, such as following depletion of the current IV fluid bag. In this regard, the timing with which the replacement IV fluid bag must be prepared and delivered may be difficult to mesh with the depletion of the current IV fluid bag. For example, the physician's orders may indicate that an IV fluid bag is to be prepared and administered to the patient in accordance with a predefined schedule, such as every four hours, every eight hours, or the like. As such, the pharmacy may prepare the IV fluid bag in accordance with the predefined schedule. However, the rate at which the patient actually receives the IV fluid may vary from that anticipated by the physician such that the patient may not require replacement IV fluid bags as frequently as anticipated by the predefined schedule. Thus, the replacement IV fluid bags prepared by the pharmacy in accordance with the predefined schedule may be delivered to the nurses responsible for the patient's care, but may then be stored awaiting the completion of the prior IV fluid bag prior to administration of the replacement IV fluid bag. Depending upon the length of time that the replacement IV fluid bag is stored, the replacement IV fluid bag may sometime become outdated.

In other instances, IV fluid bags are not prepared and delivered in accordance with a predefined schedule, but are replaced upon request by a nurse responsible for a patient's care. In this regard, a nurse may monitor the IV fluid intake of a patient and may request that the pharmacy prepare and deliver a replacement IV fluid bag, such as in an instance in which the administration of the current IV fluid bag is near completion. However, a nurse generally has many responsibilities in addition to monitoring the IV fluid intake of a patient and, as such, may be challenged to notify the pharmacy of a need to prepare a replacement IV fluid bag at the proper time, that is, not too soon such that the replacement IV fluid bag must be stored for too long of time prior to administration to the patient and too late such that the pharmacy will not have sufficient time to prepare and deliver the IV fluid bag prior to the completion of the administration of the prior IV fluid bag. As such, the timely preparation and delivery of IV fluid bags to the patient remains a challenge.

BRIEF SUMMARY

An IV fluid monitoring system and method are provided in accordance with an example embodiment in order to facilitate notification that an IV fluid bag may soon need to be replaced. As such, a replacement IV fluid bag may be prepared and delivered in a timely manner based upon the notification so as to reduce instances in which replacement IV fluid bags are prepared either too soon or too late too relative to the depletion of the current IV fluid bag. A method and apparatus are also provided in accordance with an example embodiment in order to facilitate preparation of an IV fluid bag. In his regard, the method and apparatus of an example embodiment may facilitate preparation of an IV fluid bag in such a manner that the resulting IV fluid bag is configured to assist in the notification that the administration of the IV fluid bag is nearing completion.

An IV fluid monitoring system is provided in accordance with an example embodiment and includes a bag sensing element carried by an IV fluid bag that is configured to store IV fluid. The IV fluid monitoring system further includes first and second sensing elements positioned on opposite sides of the IV fluid bag and configured to interact with the bag sensing element. The first and second sensing elements are physically separate from the IV fluid bag. The bag sensing element and the first and second elements are positioned such that a line of sight between at least the first sensing element and the bag sensing element extends through the IV fluid within the IV fluid bag in an instance in which the IV fluid bag is in a filled state.

The bag sensing element and the first and second sensing elements of one embodiment are positioned such that a line of sight between the second sensing element and the bag sensing element does not extend through the IV fluid within the IV fluid bag in an instance in which the IV fluid bag is in the filled state. The bag sensing element and the first and second sensing elements may be positioned in accordance with one embodiment such that the line of sight between the first sensing element and the bag sensing element extends through less IV fluid within the IV fluid bag in an instance in which the IV fluid bag is in a replacement requisition state than in an instance in which the IV fluid bag is in the filled state.

The IV fluid monitoring system of one embodiment may also include a clip member having first and second arms positioned on opposite sides of the IV fluid bag. The first and second arms carry the first and second sensing elements, respectively. The IV fluid monitoring system of one embodiment may also include a monitor communicably connected to at least one of the bag sensing element or the first and second sensing elements. The monitor is configured to determine a replacement requisition state of the IV fluid bag based upon information provided by at least one of the bag sensing element or the first and second sensing elements. A monitor may be configured to provide a notification regarding the replacement requisition state of the IV fluid bag. For example, the monitor may be configured to provide the notification to a pharmacy to initiate preparation of another IV fluid bag. The bag sensing element may include a radio frequency (RF) tag and the first and second sensing elements may RF readers.

In another embodiment, a method of monitoring IV fluid during delivery to a patient includes communicating with at least one of a bag sensing element or first and second sensing elements while IV fluid is delivered from an IV fluid bag to the patient. The IV fluid bag carries the bag sensing element. The first and second sensing elements are physically separate from the IV fluid bag and are positioned on opposite sides of the IV fluid bag during the delivery of the IV fluid. The bag sensing element and the first and second sensing elements are positioned such that a line of sight between at least the first sensing element and the bag sensing element extends through the IV fluid within the IV fluid bag in an instance in which the IV fluid bag is in a filled state. The method of this embodiment also determines a replacement requisition state of the IV fluid bag based upon information provided by the at least one of the bag sensing element or the first and second sensing elements.

The method of one embodiment may also include providing a notification regarding the replacement requisition state of the IV fluid bag. For example, the method may provide the notification to a pharmacy to initiate preparation of another IV fluid bag.

In a further embodiment, an apparatus for preparing an IV fluid bag is provided that includes a processor configured to determine a prescribed drip rate for a patient. The processor of this embodiment is also configured to determine a preparatory time period in which another IV fluid bag is to be prepared. Further, the processor of this embodiment is configured to determine a fluid level of the IV fluid bag at which the IV fluid remaining within the IV fluid bag will require at least the preparatory time period to be administered at the prescribed drip rate in order to facilitate placement of a bag sensing element, such as a radio frequency tag, upon the fluid bag based upon the fluid level.

The apparatus of one embodiment may also include a scale configured to be positioned in proximity to the IV fluid bag to provide an indication of the fluid level while placing the bag sensing element upon the IV fluid bag. The apparatus of one embodiment may also include a light source configured to illuminate a portion of the IV fluid bag to provide an indication of the fluid level while placing the bag sensing elements upon the IV fluid bag. The processor of one embodiment may also be configured to receive a notification that a prior IV fluid bag of the patient has reached a replacement requisition state in which the IV fluid in the prior IV fluid bag is no greater than the fluid level based upon which the bag sensing element is placed.

In yet another embodiment, a method of preparing an IV fluid bag is provided that includes determining a prescribed drip rate for a patient. The method of this embodiment lo determines a preparatory time period in which another IV fluid bag is to be prepared. The method of this embodiment also determines a fluid level of the IV fluid bag at which the IV fluid remaining within the IV fluid bag will require at least the preparatory time period to be administered at the prescribed drip rate in order to facilitate placement of a bag sensing element, such as a radio frequency tag, upon the IV fluid bag based upon the fluid level.

The method of one embodiment may also include providing an indication of the fluid level while placing the bag sensing element upon the IV fluid bag. The method of one embodiment may also include receiving a notification that a prior IV fluid bag of the patient has reached a replacement requisition state in which the IV fluid in the prior IV fluid bag is no greater than the fluid level based upon which the bag sensing element is placed.

BRIEF DESCRIPTION OF THE SEVERAL VIEWS OF THE DRAWINGS

Figure 1:
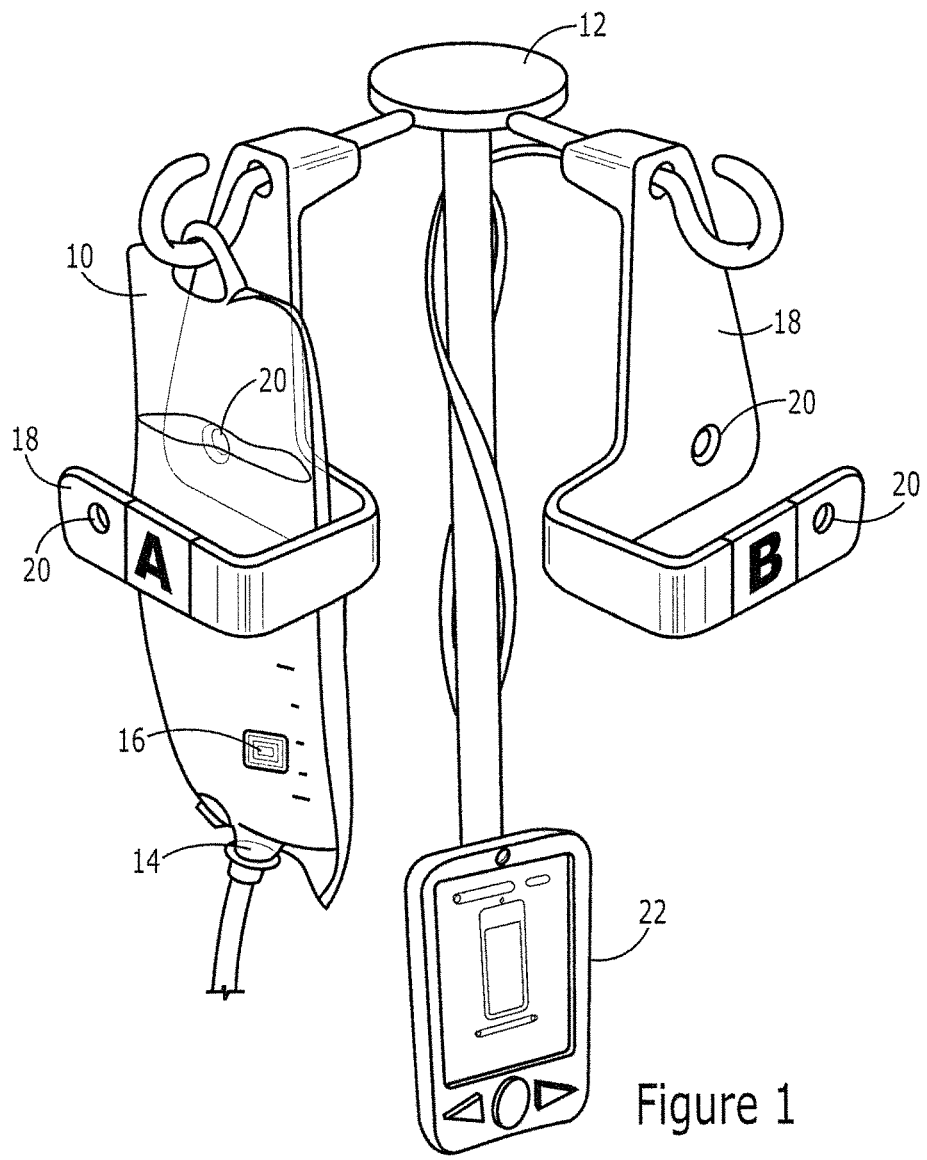
Figure 2:
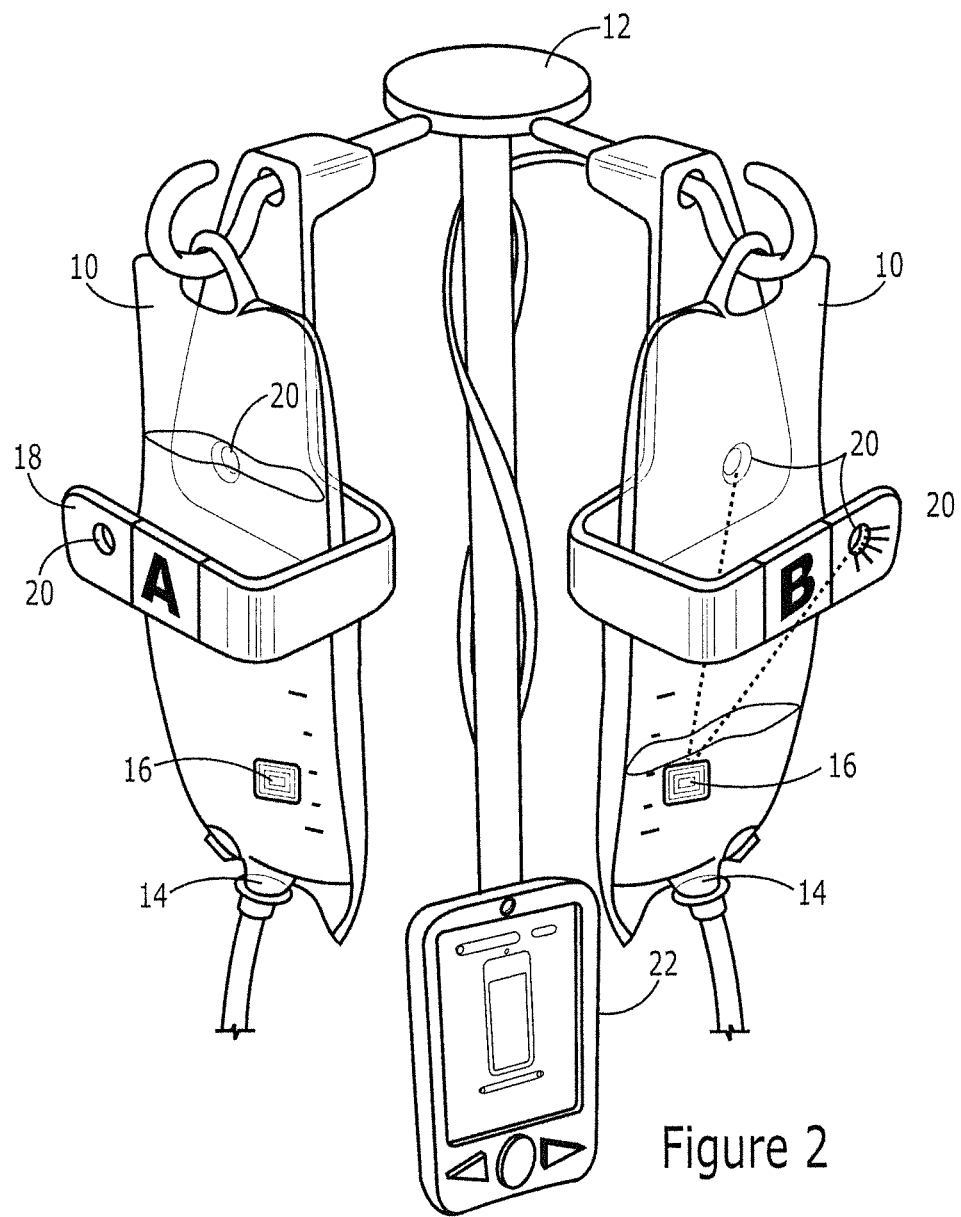
Figure 3:
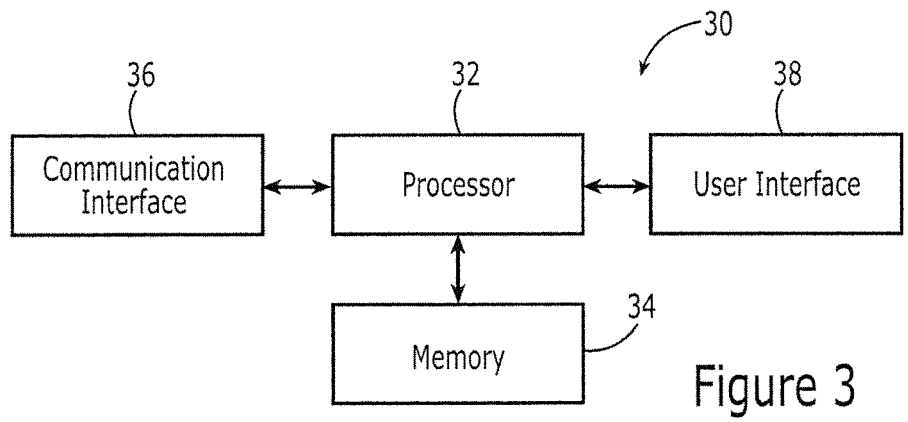
Figure 4:
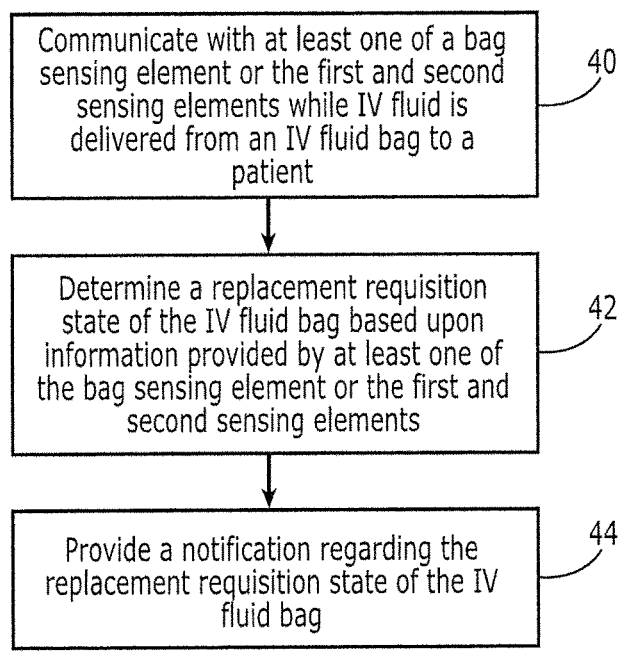
Figure 5:
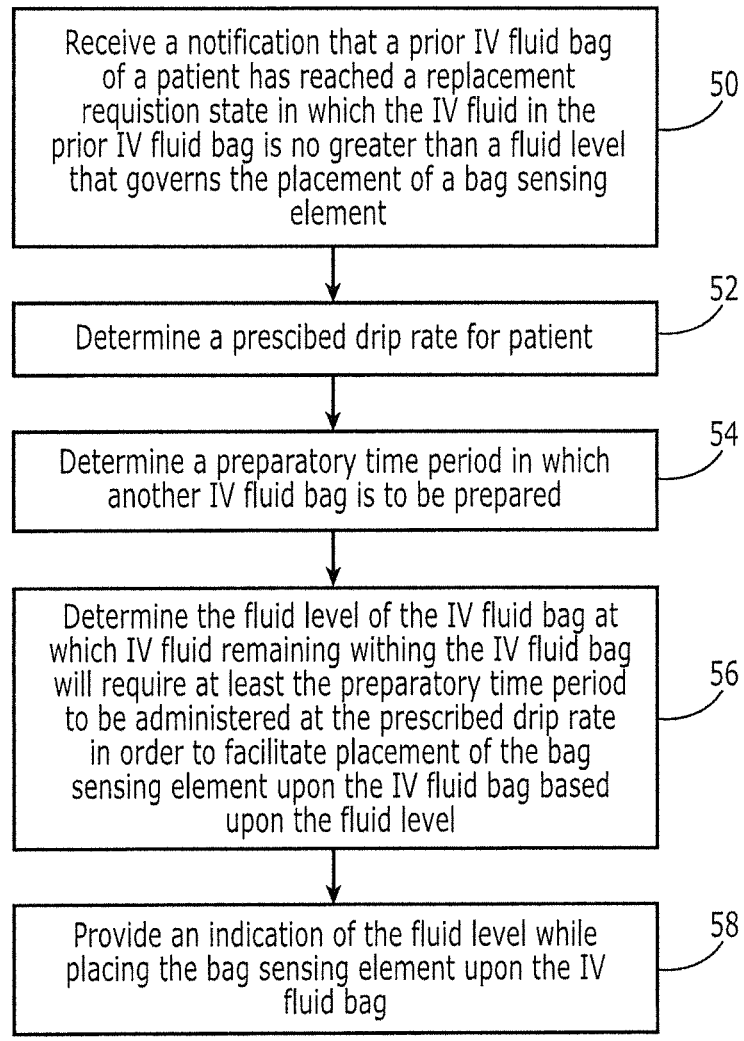
Figure 6:
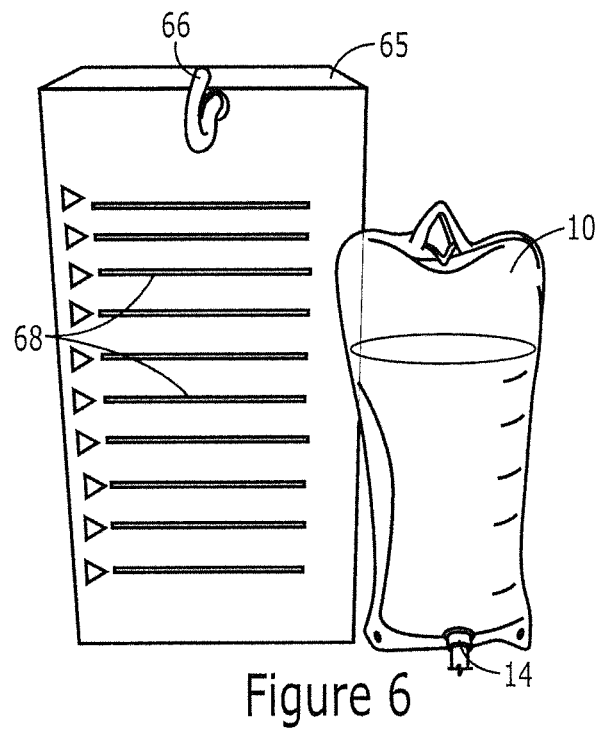
Figure 7:
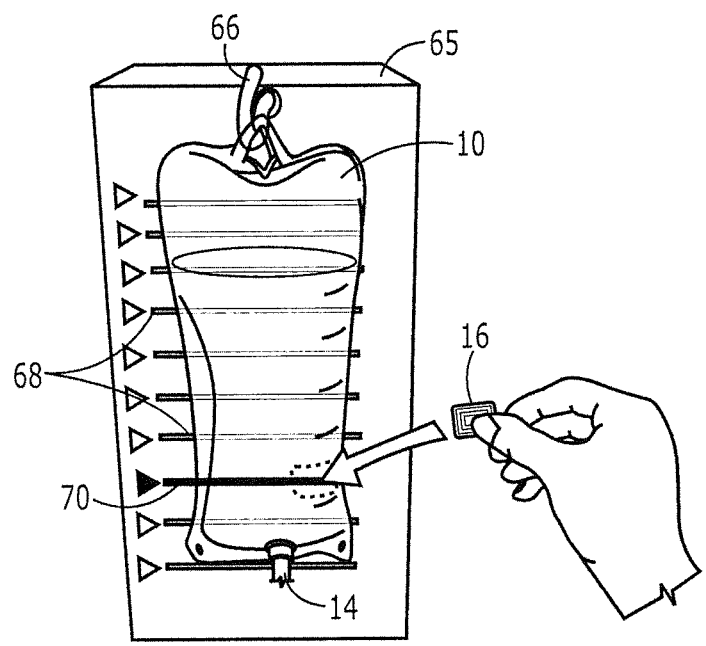
Figure 8:
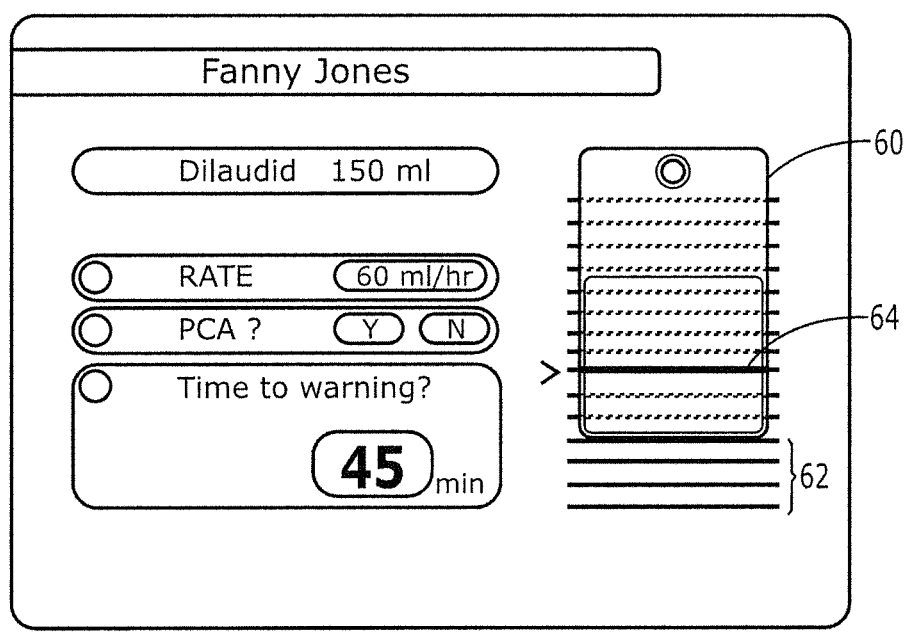

Having thus described example embodiments of the invention in general terms, reference will now be made to the accompanying drawings, which are not necessarily drawn to scale, and wherein:

FIG. 1 is a perspective view of at least a portion of an IV fluid monitoring system in accordance with an example embodiment of the present invention;

FIG. 2 is another perspective view of at least a portion of an IV fluid monitoring system in accordance with an example embodiment of the present invention;

FIG. 3 is a block diagram of a computing device that may be specifically configured in accordance with an example embodiment of the present invention;

FIG. 4 is a flow chart illustrating operations performed, such as by the computing device of FIG. 3, in order to monitor IV fluid during delivery to a patient in accordance with an example embodiment of the present invention;

FIG. 5 is a flow chart illustrating operations performed, such as by the computing device of FIG. 3, in conjunction with the preparation of an IV fluid bag in accordance with an example embodiment of the present invention;

FIG. 6 is a perspective view illustrating a scale to facilitate the placement of a bag sensing element upon the IV fluid bag in accordance with example embodiment of the present invention;

FIG. 7 a perspective view of the scale of FIG. 6 illustrating the illumination of an indication of the fluid level during placement of a bag sensing element upon the IV fluid bag in accordance with an example embodiment of the present invention; and FIG. 8 is an example of a screen display that may be presented during the preparation of an IV fluid bag in accordance with an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Referring now to FIG. 1, an intravenous (IV) fluid monitoring system in accordance with an example embodiment of the present invention is illustrated. As shown, the IV fluid monitoring system may include one or more IV fluid bags 10 configured to store and to controllably dispense an IV fluid. In this regard, the IV fluid bags may be configured to store and dispense any of a wide variety of IV fluids. The IV fluid bags may define an outlet 14 for controllably releasing the IV fluid, such as through a conduit, such a tube or the like, for delivery to a patient. In one embodiment, the IV fluid bags may be hung or otherwise temporarily affixed to an IV pole 12 for facilitating the gravity-fed delivery of the IV fluid to the patient. However, the IV fluid bags may be mounted relative to the patient in a variety of other manners, such as by being mounted to the patient's bed, to a wall in proximity to the patient or the like.

During delivery of the IV fluid to the patient, the level of the IV fluid will gradually decrease within the IV fluid bag 10. In at least some instances, the IV fluid delivered from the current IV fluid bag to the patient is not the last IV fluid to be delivered to the patient and, instead, a replacement IV fluid bag is to be prepared to continue the delivery of the IV fluid following completion of the current IV fluid bag. In order to provide a notification regarding the preparation of a replacement IV fluid bag, the IV fluid monitoring system of an example embodiment may include a bag sensing element 16 carried by the IV fluid bag. The IV fluid monitoring system may also include first and second sensing elements 20 positioned on opposite sides of the IV fluid bag and configured to interact with the bag sensing element. The bag sensing element and the first and second sensing elements may be configured in various manners. For example, the bag sensing element may be a radio frequency (RF) tag, and the first and second sensing elements may be RF readers configured to communicate with the bag sensing element. Alternatively, the bag sensing element and the first and second sensing elements may be capacitive sensors that are configured to interact with one another in order to determine the capacitance therebetween. Further, the bag sensing element and the first and second sensing elements may be optical elements, with the first and second sensing elements comprising light transducers and the bag sensing element comprising an optical reflector such that optical signals generated by the first and second sensing elements may be at least partially reflected by the bag sensing element and captured by the first and second sensing elements.

As noted above, the bag sensing element 16 is carried by the IV fluid bag 10. However, the first and second sensing elements 20 are physically separate from the IV fluid bag and are not carried by the IV fluid bag. In this regard, the first and second sensing elements may be physically separate from the IV fluid bag by being spaced apart therefrom. Alternatively, the first and second sensing elements may be positioned in physical contact with the IV fluid bag, but may remain physically separate from the IV fluid bag since the first and second sensing elements are not attached to or otherwise carried by the IV fluid bag and are, instead, carried by another element.

In an example embodiment, the IV fluid monitoring system includes a clip member 18 having first and second arms positioned on opposite sides of the IV fluid bag 10, as shown in FIG. 1. The first and second arms are configured to carry the first and second sensing elements 20, respectively. The first and second sensing elements may be carried by the first and second arms, respectively, and, as such, may be maintained in a predefined position relative to the bag sensing element 16. For example, the first and second sensing elements may be aligned with the bag sensing element or may be offset or positionally displaced from the bag sensing element in other embodiments, such as shown in FIG. 1.

In the illustrated embodiment, the clip member 18 is configured to be carried by the IV pole 12. For example, the clip member may include a hanger portion configured to be mounted upon a respective hook that extends radially outward from the IV pole and upon which the IV fluid bags 10 may also be hung. As such, the IV fluid bags of this embodiment may be hung such that the IV fluid bag is positioned between the first and second arms of the clip member and, as a result, between the first and second sensing elements 20 carried by the first and second arms, respectively, of the clip member.

The bag sensing element 16 and the first and second sensing elements 20 are positioned relative to the IV fluid bag 10 and may be configured to communicate with one another in such a manner that the interaction between first sensing element and the bag sensing element and between the second sensing element and the bag sensing element differs from one another, such as by at least a predefined difference, in an instance in which the IV fluid bag is in one of a filled state or a replacement requisition state, but is similar to one another, such as by differing by less than a predetermined amount, in the other of the filled state or the replacement requisition state. For example, the bag sensing element and the first and second sensing elements may be positioned relative to the IV fluid bag such that the path of communication between the first sensing element and the bag sensing element passes through the IV fluid in an instance in which the IV fluid bag is in the filled state which alters, such as attenuates, the signals transmitted therebetween, while the path of communication of the second sensing element and the bag sensing element passes through less and, in some instances, no IV fluid in the filled state such that the communications therebetween is not altered, at least not as much. Conversely, in the replacement requisition state, the first sensing element and the bag sensing element and the second sensing element and the bag sensing element communicate along paths that pass through comparable amounts of IV fluid, such as by passing through no IV fluid, such that the communications between the first and second sensing elements and the bag sensing element are altered in the same or a similar manner, such as by experiencing no attenuation due to the IV fluid.

Thus, the IV fluid monitoring system and method of one embodiment may detect the state of the IV fluid bag 10, such as by detecting the filled state or the replacement requisition state of the IV fluid bag, based upon the signal strength, or a change in the signal strength, of the signals exchanged between the first and second sensing elements 20 and the bag sensing element 16. For example, the IV fluid monitoring system and method may detect the state of the IV fluid bag based upon similarities or differences between the signal strength of the signals exchanged between the first sensing element and the bag sensing element and between the second sensing element and the bag sensing element.

For example, the bag sensing element 16 and the first and second sensing elements 20 of one embodiment are positioned such that a line of sight between at least the first sensing element and the bag sensing element extends through the IV fluid within the IV fluid bag 10 in an instance in which the IV fluid bag is in a filled state. A line of sight between the first or second sensing element and the bag sensing element may be a line or path therebetween via which the respective one of the first or second sensing element and the bag sensing element communicate directly with one another (at least for the majority of the direct communications therebetween). By way of example, but not of limitation, the line of sight of one embodiment may be a straight line between the respective one of the first or second sensing element and the bag sensing element. Additionally, as the line of sight refers to the path of communication between the respective one of the first or second sensing element and the bag sensing element, the respective one of the first or second sensing element and the bag sensing element need not necessarily be capable of being visibly seen along the line of sight, such as in instances in which the IV fluid is opaque.

In the embodiment of FIG. 2, for example, the first sensing element 20 may be positioned rearward of the IV fluid bag 10 so as to be closer to the IV pole 12 than the second sensing element. As such, in an instance in which the IV fluid bag is in a filled state with the IV fluid filling a majority of the IV fluid bag, a line of sight extending from the first sensing element to the bag sensing element extends through the IV fluid. Conversely, a line of sight from the second sensing element to the bag sensing element extends through less, if any, IV fluid within the IV fluid bag than the line of sight between the first sensing element and the bag sensing element. In the embodiment illustrated in FIG. 2, for example, a line of sight between the second sensing element and the bag sensing element may not extend through any IV fluid within the IV fluid bag since the line of sight between the second sensing element and the bag sensing element may be exterior to the IV fluid bag.

As the IV fluid is delivered to the patient, however, the level of the IV fluid within the IV fluid bag 10 is reduced. In an instance in which the IV fluid bag is to be replaced upon the delivery of its contents to the patient, a replacement requisition state may be defined which identifies a level of IV fluid within the IV fluid bag at which the replacement IV fluid bag should be requested such that the pharmacy is provided with sufficient time to prepare and deliver the replacement IV fluid bag prior to the exhaustion of the current IV fluid bag, but close enough in time to the exhaustion of the current IV fluid bag such that the replacement IV fluid bag does not become outdated prior to its administration to the patient. Further details regarding the fluid level that defines the replacement requisition state are provided below. Typically, however, the bag sensing element 16 is carried by the IV fluid bag at a position that is based upon the fluid level within the IV fluid bag that defines the replacement requisition state. As such, the bag sensing element and the first and second sensing elements 20 may be positioned such that the line of sight between the first sensing element and the bag sensing element extends through less IV fluid and, in some embodiments, through no IV fluid, within the IV fluid bag in an instance in which the IV fluid bag is in the replacement requisition state than in an instance in which the IV fluid bag is in the filled state. As shown in FIG. 2, for example, the IV fluid bag associated with the clip member 18 designated B has a fluid level consistent with the replacement requisitioned state, while the IV fluid bag associated with the clip member designated A has a fluid level consistent with the filled state. As shown by the dashed lines in FIG. 2 in relation to the fluid bag associated with clip member B, the line of sight from the first sensing element to the bag sensing element no longer extends through IV fluid within the IV fluid bag as a result of the reduction in the level of IV fluid within the IV fluid bag.

In one embodiment, the first and second sensing elements 20 and the bag sensing element 16 may detect the other's presence once the IV fluid bag 10 has been positioned relative to the first and second sensing elements, such as by being hung upon the IV pole 12. The first and second sensing elements and the bag sensing element may detect the other's presence in various manners including, for example, based upon proximity-based communications, e.g., RF communications, therebetween. Once the first and second sensing elements and the bag sensing element have detected the other's presence, the first and second sensing elements and the bag sensing element may communicate with one another so as gather information from which the level of the IV fluid may be determined. As such, the first and second sensing elements and the bag sensing element of this embodiment may commence communications and determine the level of the IV fluid in an autonomous manner without requiring input or direction by a nurse.

Based upon the interaction between the bag sensing element 16 and the first and second sensing elements 20, information may be provided from which the level of IV fluid within the IV fluid bag 10 may be determined. For example, in instances in which the interaction, such as the signals exchanged, between the first sensing element and the bag sensing element is dramatically different than the interaction, such as the signals exchanged, between the second sensing element and the bag sensing element, a determination may be made that the IV fluid bag is in a filled state. In this regard, the IV fluid within the IV fluid bag in the filled state may alter the interaction, such as the signals exchanged, between the first sensing element and the bag sensing element in a different manner than the interaction, such as the signals exchanged, between the second sensing element and the bag sensing element. Alternatively, in the replacement requisition state, the manner in which the IV fluid within the IV fluid bag will alter the interaction, such as the signals exchanged, between the first sensing element and the bag sensing element and between the second sensing element and the bag sensing element may differ to a much lesser degree, if any. Thus, by comparing the interaction between the first sensing element and the bag sensing element and between the second sensing element and the bag sensing element, a determination may be made as to whether the IV fluid bag is in a filled state, such as in an instance in which the difference between the interactions exceeds a predefined threshold, or is in a replacement requisition state, such as in an instance in which the difference between interactions is less than the predefined threshold.

In the illustrated embodiment, the IV fluid monitoring system may also include a monitor 22 that is communicably connected to at least one of the bag sensing element 16 or the first and second sensing elements 20. As such, the monitor may be provided with information regarding the interactions between the first and second sensing elements and the bag sensing element, such as information regarding signals exchanged between the first and second sensing elements and the bag sensing element. In the illustrated embodiment, the monitor is configured to communicate with the first and second sensing elements, although the monitor may also or alternatively communicate with the bag sensing element. As shown, the monitor may communicate with the first and second sensing elements via a wired connection. Alternatively, the first and second sensing elements may communicate with the monitor via a wireless connection, such as a Bluetooth or other proximity-based wireless communication techniques.

In one embodiment, the monitor 22 may collect the information provided by the bag sensing element 16 and/or the first and second sensing elements 20 and may provide the information to another computing device, such as a personal computer, a server or the like, for analysis, storage and reporting. Alternatively, the monitor may analyze the information provided by the bag sensing element and/or the first and second sensing elements and may determine the state of the IV fluid bag 10. For example, the monitor of one embodiment may be configured to determine that the IV fluid bag is in a filled state, such as in an instance in which the interaction, such as the signals exchanged, between the first and second sensing elements and the bag sensing element differ by more than a predefined threshold. Alternatively, the monitor may be configured to determine that the IV fluid bag is in a replacement requisition state, such as in an instance in which the interaction, such as the signals exchanged, between the first and second sensing elements and the bag sensing element differ by no more than a predefined threshold.

The monitor 22 may be configured to provide a notification regarding the state of the IV fluid bag 10 and, more particularly, the replacement requisition state of the IV fluid bag. In one embodiment, for example, the monitor may be configured to provide an audible and/or visual notification, such as to the nurse responsible for the care of the patient in an instance in which the IV fluid bag is in a replacement requisition state. Thus, a nurse may take note of the replacement requisition state of the IV fluid and may contact the pharmacy to have a replacement IV fluid bag prepared. Alternatively, or additionally, the monitor may be configured to provide a notification to the pharmacy to request the preparation of a replacement IV fluid bag in response to a determination that the current IV fluid bag is in a replacement requisition state. The monitor of an example embodiment may also be configured to receive input from the nurse or other healthcare practitioner that may be relevant to the preparation of an IV fluid bag. For example, a nurse may provide input via the monitor indicating that although the IV fluid bag is in a replacement requisition state, the preparation of a replacement IV fluid bag should be delayed or cancelled so as to effectively place a hold upon an order for a replacement IV fluid bag, such as in an instance in which the nurse is aware that the patient is being discharged or is otherwise not going to utilize a replacement IV bag for at least some time period. In this instance, the input provided by the nurse or other healthcare practitioner may be relayed by the monitor to the pharmacy so as to avoid the unnecessary preparation of a replacement IV fluid bag in an instance in which the replacement IV fluid bag would not be utilized, at least not in a timely manner. As such, the monitor of one embodiment permits a nurse to provide input that overrides a prior order for a replacement IV fluid bag.

The monitor 22 may be connected to an electrical power source, such as a wall outlet. However, the monitor may also be battery powered such that in instances in which the patient is mobile and has moved away from the electrical power source, such as an instance in which the patient walks down the hall, the monitor may continue to monitor the IV fluid level of the IV fluid bag 10. In order to conserve power, the monitor may be configured to detect the presence of a nurse or other healthcare practitioner, such as by detecting that an RF or other type of tag carried by the nurse is in proximity to the monitor. In an instance in which the RF or other type of tag is detected by the monitor, the monitor may enter an active state in which the display is activated and information regarding the state of the IV fluid bag is provided and input from the nurse is received. However, in instances in which the monitor does not detect an RF or other type of tag carried by the nurse, the monitor may remain in a dormant state, at least until input is provided to the monitor that causes the monitor to become active. In the dormant state, the display of the monitor may be dimmed or extinguished to conserve power, while continuing to monitor the fluid level of the IV fluid bag as described above.

The monitor 22 may be configured as an apparatus 30 embodied by a computing device, such as a tablet computer, a smartphone, a personal digital assistant (PDA) or the like. Although the monitor may be configured in various manners, the monitor of one embodiment may be configured as shown in FIG. 3 so as to include or otherwise be in communication with a processor 32 that is configurable to perform functions in accordance with one or more example embodiments disclosed herein. In this regard, the processor may be configured to perform and/or control performance of one or more functionalities of the apparatus (e.g., functionalities of a computing device on which the apparatus may be implemented) in accordance with various example embodiments, and thus may provide means for performing functionalities of the apparatus (e.g., functionalities of a computing device on which the apparatus may be implemented) in accordance with various example embodiments. The processor may be configured to perform data processing, application execution and/or other processing and management services according to one or more example embodiments.

In some example embodiments, the processor 32 may be in communication with or otherwise control a memory 34, a communication interface 36 and/or a user interface 38. The processor may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In some example embodiments, the processor may be configured to execute instructions stored in the memory or otherwise accessible to the processor. As such, whether configured by hardware or by a combination of hardware and software, the processor may represent an entity (e.g., physically embodied in circuitry—in the form of processing circuitry) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 34 may include one or more non-transitory memory devices such as, for example, volatile and/or non-volatile memory that may be either fixed or removable. In this regard, the memory may comprise a non-transitory computer-readable storage medium. The memory may be configured to store information, data, applications, instructions and/or the like for enabling the apparatus 30 to carry out various functions in accordance with one or more example embodiments. For example, the memory may be configured to store instructions for execution by the processor 32. As yet another alternative, the memory may include one or more databases that may store a variety of files, contents or data sets. Among the contents of the memory, applications may be stored for execution by the processor in order to carry out the functionality associated with each respective application. In some cases, the memory may be in communication with one or more of the processor, user interface 38, or communication interface 36 via a bus or buses for passing information among components of the apparatus.

The user interface 38 may be in communication with the processing circuitry 32 to receive an indication of a user input at the user interface and/or to provide an audible, visual, mechanical or other output to the user. As such, the user interface may include, for example, a keyboard, a mouse, a joystick, a display, a touch screen display, a microphone, a speaker, a light emitting diode (LED), a lighting device, an electronic sensor for capturing human body movements, and/or other input/output mechanisms. Via the user interface, the monitor 22 of one embodiment may receive input from a nurse and may provide a notification.

The communication interface 36 may include one or more interface mechanisms for enabling communication with other devices and/or networks, such as for supporting communication with bag sensing element 16 and/or the first and second sensing elements 20, with the pharmacy and/or with an RF or other type of tag associated with a nurse. In some cases, the communication interface may be any means such as a device or circuitry embodied in either hardware, or a combination of hardware and software that is configured to receive and/or transmit data from/to a network and/or any other device or module in communication with the processing circuitry 32, either wirelessly or via a wireline network.

Referring now to FIG. 4, the operations performed by a computing device that embodies the monitor 22 of one embodiment for monitoring an IV fluid level are provided. As shown in block 40 of FIG. 4, the monitor, such as the processor 32, the communication interface 36 or the like, may communicate with at least one of the bag sensing element 16 or the first and second sensing elements 20 while IV fluid is delivered from the IV fluid bag 10 to a patient. In the illustrated embodiment, for example, the monitor is configured to communicate with the first and second sensing elements. The monitor may communicate with the first and second sensing elements so as to obtain information regarding the interaction of the first and second sensing elements with the bag sensing element, and, in one embodiment, may receive information regarding signals exchanged between the first and second sensing elements and the bag sensing element for purposes of making a comparison therebetween.

As shown in block 42 of FIG. 4, the monitor 22, such as the processor 32 or the like, may be configured to determine the replacement requisition state of the IV fluid bag 10 based upon the information provided by at least one of the bag sensing element 16 or the first and second sensing elements 20. As described above, the monitor, such as the processor, may determine that the IV fluid bag is in the replacement requisition state in an instance in which the differences between the interactions, such as the signals exchanged, between the first and second sensing elements and the bag sensing element are less than a predefined threshold. In an instance in which the monitor determines that the IV fluid bag is in a replacement requisition state, the monitor, such as the processor, the communications interface 36 or the like, may be configured to provide a notification regarding the replacement requisition state of the IV fluid bag, such as via the user interface 38, e.g., a display, for notification of the nurse responsible for the patient's care and/or via a signal transmitted to the pharmacy to request preparation of a replacement IV fluid bag. See block 44 of FIG. 4.

By determining the replacement requisition state, the IV fluid monitoring system and method of this embodiment may assist the nurse or other healthcare practitioner in identifying the need to initiate preparation of a replacement IV fluid bag 10. As such, the replacement IV fluid bag may be prepared in a timely manner, such that the IV fluid bag may be prepared and delivered by the time that the replacement IV fluid bag is needed for the patient. However, the replacement IV fluid bag is not delivered too far in advance. As such, the replacement IV fluid bag need not be stored for an excessive period of time, thereby reducing the risk that the replacement IV fluid bag will become outdated so as to correspondingly improve the efficiency with which IV fluid bags are replaced.

As described above, the bag sensing element 16 is placed upon the IV fluid bag 10 at a position that is determined based upon the fluid level within the IV fluid bag that defines the replacement requisition state. In this regard, the fluid level that defines the replacement requisition state is that fluid level that provides sufficient time prior to completion of the delivery of the IV fluid from the current IV fluid bag to have another replacement IV fluid bag prepared and delivered to the patient. As such, the fluid level that defines a replacement requisition state is based upon a combination of the rate at which the IV fluid is being delivered to the patient as well as the time required to prepare and deliver a replacement IV fluid bag.

As shown in FIG. 5, a method of preparing an IV fluid bag 10 is provided in accordance with an example embodiment of the present invention and may include determining a prescribed drip rate for a patient which may, in combination with the volume of IV fluid remaining with the IV fluid bag, define the remaining time period for delivery of the IV fluid from the current IV fluid bag. See block 52. The method of this embodiment may also determine the preparatory time required for another IV fluid bag to be prepared. See block 54. In this regard, the preparatory time period may be based upon the time required to prepare and deliver a replacement IV fluid bag and, for example, may take into account the staffing of the pharmacy at which the replacement IV fluid bag is to be prepared, the relative level of business of the pharmacy at which the replacement IV fluid bag is prepared, the delivery time or delivery schedule for replacement IV fluid bags and the like.

Although the method may be manually implemented, the method of one embodiment may be implemented by an apparatus 30 embodied by a computing device, such as of the type shown in FIG. 3. In this regard, the computing device may include a processor 32 configured to determine the prescribed drip rate for a patient and the preparatory time period in which another IV fluid bag 10 is to be prepared. The processor may determine the prescribed drip rate and the preparatory time period in various manners, but, in one embodiment, determines the prescribed drip rate and the preparatory time period based upon predefined values stored, for example, by memory 34. Additionally or alternatively, the computing device, such as the processor, may receive input, such as the drip rate, volume of IV fluid, etc., from other computer systems, such as other pharmacy systems, and then proceed to prepare the IV fluid bag based upon these inputs. The method, as shown in block 56 of FIG. 5, may then determine the fluid level of the IV fluid bag at which the IV fluid remaining within the IV fluid bag will require at least the preparatory time period to be administered at the prescribed drip rate. In an embodiment in which the method is computer implemented, the computing device, such as the processor, may determine the fluid level associated with the replacement requisition state. The fluid level that is determined in this manner may define the fluid level associated with the replacement requisition state as this fluid level will permit a replacement IV fluid bag to be prepared in a timely manner prior to completing delivery of the IV fluid from the current IV fluid bag to the patient.

The determination of the fluid level associated with the replacement requisition state may facilitate placement of the bag sensing element 16 upon the IV fluid bag 10. In one embodiment, the bag sensing element may be placed upon the IV fluid bag at a location equal to the fluid level associated with the replacement requisition state. Alternatively, the bag sensing element may be placed upon the IV fluid bag in another position relative to the fluid level associated with the replacement requisition state, such as another position having a predefined positional relationship to the fluid level associated with the replacement requisition state. In either instance, the bag sensing element may have a predefined position relative to the fluid level associated with the replacement requisition state.

In order to facilitate the placement of the bag sensing element 16 upon the IV fluid bag 10, an indication may be provided of the fluid level associated with the replacement requisition state while the bag sensing element is placed upon the IV fluid bag. See block 58 of FIG. 5. Various types of indications may be provided of the fluid level associated with the replacement requisition state while the bag sensing element is placed upon the IV fluid bag. In one embodiment, for example, a scale 65 may be provided, such as shown in FIG. 6, with predefined indications 68 of a plurality of different fluid levels. The scale may be positioned in proximity to the IV fluid bag, such as by hanging or otherwise temporarily affixing the IV fluid bag relative to the scale. For example, the IV fluid bag may be hung from a hook 66 positioned above the plurality of predefined indications. The bag sensing element may then be placed upon the IV fluid bag at a location based upon the predefined indications of the plurality of different fluid levels provided by the scale. For example, the bag sensing element may be placed upon the IV fluid bag at a location defined by, such as in alignment with, a respective one of the predefined indications provided by the scale.

In one embodiment, for example, an indication of the fluid level associated with the replacement requisition state is provided during placement of the bag sensing element 16 upon the IV fluid bag 10 by illuminating a portion of the IV fluid bag to provide the indication. As such, a light source may be provided to illuminate a portion of the IV fluid bag in order to provide the indication of the fluid level. With respect to the scale of FIG. 7, for example, one of the indications, namely, predefined indication 70, may be illuminated with the bag sensing element then being placed upon the IV fluid bag and adhered thereto, such as with adhesive, so as to be in a predefined position, such as in alignment, with the indication of the fluid level associated with the replacement requisition state. In other embodiments that include a light source to illuminate a portion of the IV fluid bag so as to provide an indication of the fluid level associated with the replacement requisition state, the light source may be differently configured and may illuminate the portion of the IV fluid bag in a different manner.

As described above, the pharmacy, such as a computing device utilized by the pharmacy and, more particularly, the processor 32, the communication interface 36 or the like, may receive a notification that a prior IV fluid bag 10 of a patient has reached a replacement requisition state. See block 50 of FIG. 5. In this regard, the notification may be provided by a nurse responsible for the patient's care or by a monitor 22 that is monitoring the delivery of the IV fluid to the patient. In this instance, the notification may alert the pharmacy that the IV fluid in the prior IV fluid bag is no greater than the fluid level that governs the placement of the bag sensing element 16, such as the fluid level associated with the replacement requisition state. In response to receiving the notification, the pharmacy may then prepare the replacement IV fluid bag including the attachment of a bag sensing element at a desired location upon the IV fluid bag, such as in alignment with a fluid level associated with the replacement requisition state.

The computing device may not only receive notifications that a prior IV fluid bag 10 has reached a replacement requisition state, but may, in some embodiments, receive information regarding the current state of the prior IV fluid bag even in an instance in which the prior IV fluid bag has not reached the replacement requisition state. In this regard, the monitor 22 may communicate with the computing device of a pharmacy so as to provide information regarding the delivery of IV fluid from the prior IV fluid bag. The computing device at the pharmacy may, in turn, provide information regarding the current state of the prior IV fluid bag of a patient, such as visually via a user interface 38, such as shown in FIG. 8. In this regard, the patient may be identified as well as the IV fluid and the prescribed drip rate. Additional information may also be provided, such as an indication as to whether the patient has been prescribed a patient controlled analgesia (PCA). Furthermore, an estimate of the time that remains prior to the IV fluid reaching the replacement requisition state may be provided so as to facilitate planning and work flow within the pharmacy. In order to facilitate a quick review of the information provided regarding the state of the prior IV fluid bag, a graphical representation 60 of the prior IV fluid bag, the current level of the IV fluid within the IV fluid bag, a plurality of predefined fluid levels 62 and the level 64 associated with the replacement requisition state may also be depicted by the user interface in some embodiments.

Thus, the method and apparatus of this embodiment of the present invention permit replacement IV fluid bags 10 to be prepared in an efficient manner so as to improve the workflow, both of the pharmacy and of the nursing staff in conjunction with the preparation and delivery of an IV fluid bag. Moreover, the method and apparatus of the an example embodiment may reduce instances in which replacement IV fluid bags are provided either later than is desired which may cause an interruption in the delivery of IV fluid to a patient or earlier than is desired which may, in turn, cause at least some IV fluid bags to become outdated, thereby potentially increasing the cost of patient care and decreasing the efficiency with which the patient care is delivered.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An intravenous (IV) fluid monitoring system comprising:
   a bag sensing element carried by an IV fluid bag configured to store an IV fluid; and
   first and second sensing elements positioned on opposite sides of the IV fluid bag and configured to interact with the bag sensing element, wherein the first and second sensing elements are physically separate from the IV fluid bag and the bag sensing element, wherein the bag sensing element and the first and second sensing elements are positioned such that a line of sight between the first sensing element and the bag sensing element extends through the IV fluid within the IV fluid bag in an instance in which the IV fluid bag is in a filled state, and wherein interaction between the first sensing element and the bag sensing element as defined by first signals communicated between the first sensing element and the bag sensing element differs from interaction between the second sensing element and the bag sensing element as defined by second signals communicated between the second sensing element and the bag sensing element by at least a predefined difference in an instance in which the IV fluid bag is in one of the filled state or a replacement requisition state, but interaction between the first sensing element and the bag sensing element as defined by the first signals differs from interaction between the second sensing element and the bag sensing element as defined by the second signals by less than a predetermined amount in an instance in which the IV fluid bag is in the other one of the filled state or the replacement requisition state.

2. An IV fluid monitoring system according to claim 1 wherein the bag sensing element and the first and second sensing elements are positioned such that a line of sight between the second sensing element and bag sensing element does not extend through the IV fluid within the IV fluid bag in an instance in which the IV fluid bag is in a filled state.

3. An IV fluid monitoring system according to claim 1 wherein the bag sensing element and the first and second sensing elements are positioned such that the line of sight between the first sensing element and the bag sensing element extends through less IV fluid within the IV fluid bag in an instance in which the IV fluid bag is in a replacement requisition state than in an instance in which the IV fluid bag is in the filled state.

4. An IV fluid monitoring system according to claim 1 further comprising a clip member having first and second arms configured to be positioned on opposite sides of the IV fluid bag, wherein the first and second arms carry the first and second sensing elements, respectively.

5. An IV fluid monitoring system according to claim 1 further comprising a monitor communicably connected to at least one of the bag sensing element or the first and second sensing elements, wherein the monitor is configured to determine a replacement requisition state of the IV fluid bag based upon information provided by the at least one of the bag sensing element or the first and second sensing elements.

6. An IV fluid monitoring system according to claim 5 wherein the monitor is configured to provide a notification regarding the replacement requisition state of the IV fluid bag.

7. An IV fluid monitoring system according to claim 6 wherein the monitor is configured to provide the notification to a pharmacy to initiate preparation of another IV fluid bag.

8. An IV fluid monitoring system according to claim 1 wherein the bag sensing element comprises a radio frequency (RF) tag and the first and second sensing elements comprise RF readers.

9. A method of monitoring intravenous (IV) fluid during delivery to a patient, the method comprising:
communicating with at least one of a bag sensing element or first and second sensing elements while IV fluid is delivered from an IV fluid bag to the patient, wherein the IV fluid bag carries the bag sensing element, wherein the first and second sensing elements are positioned on opposite sides of the IV fluid bag during the delivery of the IV fluid, wherein the first and second sensing elements are physically separate from the IV fluid bag and the bag sensing element, wherein the bag sensing element and the first and second sensing elements are positioned such that a line of sight between at least the first sensing element and the bag sensing element extends through the IV fluid within the IV fluid bag in an instance in which the IV fluid bag is in a filled state, and wherein interaction between the first sensing element and the bag sensing element as defined by first signals communicated between the first sensing element and the bag sensing element differs from interaction between the second sensing element and the bag sensing element as defined by second signals communicated between the second sensing element and the bag sensing element by at least a predefined difference in an instance in which the IV fluid bag is in one of the filled state or a replacement requisition state, but interaction between the first sensing element and the bag sensing element as defined by the first signals differs from interaction between the second sensing element and the bag sensing element as defined by the second signals by less than a predetermined amount in an instance in which the IV fluid bag is in the other one of the filled state or the replacement requisition state; and
determining a replacement requisition state of the IV fluid bag based upon information provided by the at least one of the bag sensing element or the first and second sensing elements.

10. An IV fluid monitoring method according to claim 9 further comprising providing a notification regarding the replacement requisition state of the IV fluid bag.

11. An IV fluid monitoring method according to claim 10 wherein providing the notification comprises providing the notification to a pharmacy to initiate preparation of another IV fluid bag.

12. An apparatus for preparing an intravenous (IV) fluid bag prior to administration to a patient, the apparatus comprising a processor configured to:
determine a prescribed drip rate for the patient;
determine a preparatory time period in which another IV fluid bag is to be prepared;
determine a fluid level of the IV fluid bag at which IV fluid remaining within the IV fluid bag will require at least the preparatory time period to be administered at the prescribed drip rate in order to facilitate placement of a bag sensing element upon the IV fluid bag based upon the fluid level; and
based upon the fluid level, cause a visible indication to be provided of a location upon the IV fluid bag at which a bag sensing element is to be placed prior to the administration of the IV fluid to the patient.

13. An apparatus according to claim 12 further comprising a scale configured to be positioned in proximity to the IV fluid bag to provide an indication of the fluid level while placing the bag sensing element upon the IV fluid bag.

14. An apparatus according to claim 12 further comprising a light source configured to illuminate a portion of the IV fluid bag to provide an indication of the fluid level while placing the bag sensing element upon the IV fluid bag.

15. An apparatus according to claim 12 wherein the processor is configured to receive a notification that a prior IV fluid bag of the patient has reached a replacement requisition state in which the IV fluid in the prior IV fluid bag is no greater than the fluid level based upon which the bag sensing element is placed.

16. An apparatus according to claim 12 further comprising a radio frequency tag that serves as the bag sensing element and is placed upon the IV fluid bag.

17. A method of preparing an intravenous (IV) fluid bag prior to administration to a patient, the method comprising:
   determining a prescribed drip rate for the patient;
   determining a preparatory time period in which another IV fluid bag is to be prepared;
   determining, by a processor, a fluid level of the IV fluid bag at which IV fluid remaining within the IV fluid bag will require at least the preparatory time period to be administered at the prescribed drip rate in order to facilitate placement of a bag sensing element upon the IV fluid bag based upon the fluid level; and
   based upon the fluid level, causing an indication to be visibly provided of a location upon the IV fluid bag at which a bag sensing element is to be placed prior to the administration of the IV fluid to the patient.

18. A method according to claim 17 wherein causing an indication to be provided comprises providing an indication of the fluid level while placing the bag sensing element upon the IV fluid bag.

19. A method according to claim 17 further comprising receiving a notification that a prior IV fluid bag of the patient has reached a replacement requisition state in which the IV fluid in the prior IV fluid bag is no greater than the fluid level based upon which the bag sensing element is placed.

20. A method according to claim 17 wherein the bag sensing element comprises a radio frequency tag.

* * * * *